(12) United States Patent
Chiba

(10) Patent No.: US 10,925,527 B2
(45) Date of Patent: *Feb. 23, 2021

(54) ENDOSCOPE APPARATUS

(71) Applicant: HOYA CORPORATION, Tokyo (JP)

(72) Inventor: Toru Chiba, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 269 days.

This patent is subject to a terminal disclaimer.

(21) Appl. No.: 15/552,604

(22) PCT Filed: Dec. 12, 2016

(86) PCT No.: PCT/JP2016/086884
§ 371 (c)(1),
(2) Date: Aug. 22, 2017

(87) PCT Pub. No.: WO2017/119239
PCT Pub. Date: Jul. 13, 2017

(65) Prior Publication Data
US 2018/0049679 A1 Feb. 22, 2018

(30) Foreign Application Priority Data
Jan. 8, 2016 (JP) .................................. 2016-002275

(51) Int. Cl.
A61B 5/1455 (2006.01)
A61B 5/1459 (2006.01)
(Continued)

(52) U.S. Cl.
CPC .......... A61B 5/1459 (2013.01); A61B 1/0002 (2013.01); A61B 1/00009 (2013.01);
(Continued)

(58) Field of Classification Search
None
See application file for complete search history.

(56) References Cited

U.S. PATENT DOCUMENTS

2010/0158330 A1* 6/2010 Guissin ............. G06K 9/00369
382/128
2013/0064436 A1 3/2013 Tanaka et al.
(Continued)

FOREIGN PATENT DOCUMENTS

JP 2012-183240 9/2012
WO 2012/153568 11/2012
(Continued)

OTHER PUBLICATIONS

International Search Report and Written Opinion in WIPO Application No. PCT/JP2016/086884, dated Feb. 21, 2017.

*Primary Examiner* — Marjan Fardanesh
(74) *Attorney, Agent, or Firm* — Greenblum & Bernstein, P.L.C.

(57) ABSTRACT

An endoscope apparatus according to an embodiment of the present invention includes: a light source apparatus; an imager that has an image sensor and generates color image data by imaging biological tissue illuminated by light emitted by the light source apparatus; and a feature amount acquisitioner that acquires a feature amount of the biological tissue based on the color image data. The feature amount acquisitioner includes: a first parameter generator that, based on the color image data, generates a first parameter that has sensitivity to a first feature amount of the biological tissue, but substantially does not have sensitivity to light scattering by the biological tissue; and a first feature amount acquisitioner that acquires the first feature amount based on the first parameter.

11 Claims, 8 Drawing Sheets

(51) Int. Cl.
    *A61B 1/00*         (2006.01)
    *A61B 1/05*         (2006.01)
    *A61B 1/06*         (2006.01)
    *A61B 1/07*         (2006.01)
    *A61B 5/145*       (2006.01)
    *A61B 5/00*         (2006.01)

(52) U.S. Cl.
    CPC .............. *A61B 1/05* (2013.01); *A61B 1/0646* (2013.01); *A61B 1/0653* (2013.01); *A61B 1/0669* (2013.01); *A61B 1/07* (2013.01); *A61B 5/14546* (2013.01); *A61B 5/14551* (2013.01); *A61B 5/14552* (2013.01); *A61B 5/7246* (2013.01); *A61B 1/00096* (2013.01); *G06T 2207/10068* (2013.01)

(56) References Cited

U.S. PATENT DOCUMENTS

2014/0316283 A1    10/2014   Kaku et al.
2016/0120449 A1     5/2016   Chiba

FOREIGN PATENT DOCUMENTS

WO       2013/111623      8/2013
WO       2014/192781    12/2014

\* cited by examiner (A)

(B)

(C)

ENDOSCOPE APPARATUS

TECHNICAL FIELD

The present invention relates to an endoscope apparatus that acquires biological information such as the concentration of a biological substance in biological tissue based on a captured image of the biological tissue.

BACKGROUND ART

An endoscope apparatus is known that includes a function for determining the concentration of a biological substance (e.g., hemoglobin) in biological tissue that is the imaging subject, based on color information in an endoscopic image. An example of this type of endoscope apparatus is disclosed in WO 2014/192781 pamphlet (called "Patent Document 1" hereinafter).

The endoscope apparatus disclosed in Patent Document 1 is an endoscope apparatus that, based on color information in two endoscopic images captured using illumination light in two types of wavelength regions in hemoglobin's absorption band of roughly 500 to 600 nm, calculates an indicator that indicates the total hemoglobin concentration and an indicator that indicates the degree of oxygen saturation.

In the absorption band of hemoglobin of roughly 500 to 600 nm, the absorption coefficient is large, and the degree of absorption changes a large amount relative to change in the degree of oxygen saturation. For this reason, it is possible to detect the distribution of the total hemoglobin concentration and the degree of oxygen saturation with high sensitivity by using an image captured using illumination light in the 500 to 600 nm band.

SUMMARY OF INVENTION

However, because absorption by hemoglobin in the 500 to 600 nm band is relatively higher than in other absorption bands, there is a problem in that when biological tissue having a high total hemoglobin concentration is observed, the amount of change in the received light amount relative to the total hemoglobin concentration and the degree of oxygen saturation decreases, and sensitivity decreases.

The present invention was achieved in light of the above-described circumstances, and an object of the present invention is to provide an endoscope apparatus that can acquire the degree of oxygen saturation of biological tissue having a high total hemoglobin concentration from image information regarding the biological tissue.

An endoscope apparatus according to an embodiment of the present invention includes: a light source apparatus; an imaging unit that generates RGB color image data by imaging biological tissue illuminated by light emitted by the light source apparatus; and a feature amount acquisition unit that acquires a feature amount of the biological tissue based on the RGB color image data. The feature amount acquisition unit calculates a first parameter that has a correlation with a degree of oxygen saturation in the biological tissue based on the RGB color image data. The first parameter is any one of [a] and [b] below.

[a] R/(R+G+B)
[b] R/W
where
R is first normal observation image data R that is an R component of normal observation image data acquired under illumination by white light.

G is second normal observation image data G that is a G component of the normal observation image data.
B is third normal observation image data B that is a B component of the normal observation image data, and
W is first special observation image data W that is a G component of RBG color image data acquired under illumination by first special light.

Also, in the above endoscope apparatus, a configuration is possible in which the feature amount acquisition unit acquires the degree of oxygen saturation based on a corrected first parameter obtained by multiplying the first parameter by a first correction value for correcting influence of a total hemoglobin concentration.

According to this configuration, it is possible to easily acquire an accurate degree of oxygen saturation that is not dependent on the total hemoglobin amount.

Also, in the above endoscope apparatus, a configuration is possible in which the feature amount acquisition unit has a first storage unit that holds a numerical value table or a function that expresses a relationship between the corrected first parameter and the degree of oxygen saturation.

Also, in the above endoscope apparatus, a configuration is possible in which the feature amount acquisition unit acquires the first correction value based on a second parameter that has a correlation with the total hemoglobin concentration.

Also, in the above endoscope apparatus, a configuration is possible in which the feature amount acquisition unit has a second storage unit that holds a numerical value table or a function that expresses a relationship between the second parameter and the total hemoglobin concentration.

Also, in the above endoscope apparatus, a configuration is possible in which the second parameter is any one of [c] to [e] below.

[c] R/G
[d] W/R
[e] W/(R+G)
where
R is the first normal observation image data R,
G is the second normal observation image data G, and
W is the first special observation image data W.

According to this configuration, it is possible to obtain an indicator of the total hemoglobin concentration by performing simple calculation on image data.

Also, in the above endoscope apparatus, a configuration is possible in which the feature amount acquisition unit acquires a total hemoglobin concentration based on the second parameter.

Also, in the above endoscope apparatus, a configuration is possible in which the first special light has a wavelength from a vicinity of an isosbestic point E1 of hemoglobin appearing at 528±5 nm to a vicinity of an isosbestic point E4 appearing at 584±5 nm.

According to this configuration, it is possible to easily acquire an accurate total hemoglobin concentration that is not dependent on the degree of oxygen saturation.

Also, in the above endoscope apparatus, a configuration is possible in which the light source apparatus includes: a white light source: and a first optical filter that extracts the first special light from white light emitted by the white light source, and the light source apparatus switches between emitting the white light and emitting the first special light.

According to this configuration, accurate degree of oxygen saturation detection can be performed by a light source apparatus that has a simple configuration including one white light source and one optical filter.

Also, in the above endoscope apparatus, a configuration is possible in which if the total hemoglobin concentration that corresponds to a value of the second parameter is greater than or equal to a predetermined value, the feature amount acquisition unit calculates the degree of oxygen saturation based on the first parameter and if the total hemoglobin concentration that corresponds to the value of the second parameter is less than the predetermined value, the feature amount acquisition unit calculates the degree of oxygen saturation based on a third parameter that reflects absorption by hemoglobin in a 500 to 600 nm absorption band.

According to this configuration, it is possible to acquire an accurate degree of oxygen saturation from image information over a wide total hemoglobin concentration range.

Also, in the above endoscope apparatus, a configuration is possible in which the light source apparatus further includes a second optical filter that extracts second special light from white light emitted by the white light source. In this case, the third parameter is N/W, where
W is the first special observation image data W, and
N is the second special observation image data N that is
  a G component of RBG color image data captured
  under illumination by the second special light, and
the second special light has a wavelength from a vicinity of an isosbestic point E2 of hemoglobin appearing at 547±5 nm to a vicinity of an isosbestic point E3 appearing at 569±5 nm.

According to this configuration, an accurate degree of oxygen saturation having little error due to scattering can be acquired with a simple configuration.

Also, in the above endoscope apparatus, a configuration is possible in which the feature amount acquisition unit has a third storage unit that holds a numerical value table or a function that expresses a relationship between the third parameter and the degree of oxygen saturation.

An endoscope apparatus according to an embodiment of the present invention includes: a light source apparatus that can generate first light and second light: an imaging unit that has an RGB color filter and can generate color image data by imaging biological tissue illuminated by light generated by the light source apparatus: and a feature amount acquisition unit that acquires a feature amount of the biological tissue based on the color image data. First transmission light is a portion of the first light that passed through an R color filter of the imaging unit, second transmission light is a portion of the second light that passed through a G color filter of the imaging unit, and absorption by hemoglobin with respect to the first transmission light and the second transmission light has a correlation with a degree of oxygen saturation. The feature amount acquisition unit has a selection unit that selects whether first image data acquired using the first transmission light or second image data acquired using the second transmission light is to be used to acquire a degree of oxygen saturation of the biological tissue, and the feature amount acquisition unit acquires the degree of oxygen saturation of the biological tissue based on the image data selected by the selection unit.

Also, in the above endoscope apparatus, a configuration is possible in which the feature amount acquisition unit can generate a first parameter that is an indicator of a degree of oxygen saturation of the biological tissue and a second parameter that is an indicator of a total hemoglobin concentration of the biological tissue, if the total hemoglobin concentration that corresponds to a value of the second parameter is greater than or equal to a predetermined value, the selection unit selects acquisition of the degree of oxygen saturation based on the first image data, and if the total hemoglobin concentration that corresponds to the value of the second parameter is less than the predetermined value, the selection unit selects acquisition of the degree of oxygen saturation based on the second image data.

Also, the above endoscope apparatus may have a configuration including a feature amount distribution image generation unit, that generates a feature amount distribution image that expresses a distribution of the feature amount in the biological tissue based on the feature amount.

Also, the above endoscope apparatus may have a configuration including an endoscope in which the imaging unit is provided in a distal end portion.

According to the configuration of an embodiment of the present invention, the degree of oxygen saturation of biological tissue having a high total hemoglobin concentration can be acquired from image information regarding the biological tissue.

DESCRIPTION OF EMBODIMENTS

Hereinafter, an embodiment of the present invention will be described with reference to the drawings.

An endoscope apparatus of an embodiment of the present invention described below is an apparatus for quantitatively analyzing biological information of a subject (e.g., a feature amount of biological tissue such as the total hemoglobin concentration or the degree of oxygen saturation) based on multiple images captured under illumination by light of different wavelength regions, and for converting the analysis results into an image and displaying the image. The spectral characteristics of blood (i.e., the spectral characteristics of hemoglobin) have a property of continuously varying according to the total hemoglobin concentration and the degree of oxygen saturation, and this property is used in the quantitative analysis of the total hemoglobin concentration and the degree of oxygen saturation performed by this apparatus.

Spectral Characteristics of Biological Tissue and Principle of Calculation of Biological Information Before giving a description of the detailed configuration of the endoscope apparatus according to this embodiment of the present invention, the following describes the spectral characteristics of hemoglobin and the principle of the calculation of a feature amount of biological tissue (biological information), such as the degree of oxygen saturation, according to this embodiment of the present invention.

Calculation Using Absorption in 500 to 600 nm Band

Figure 1:
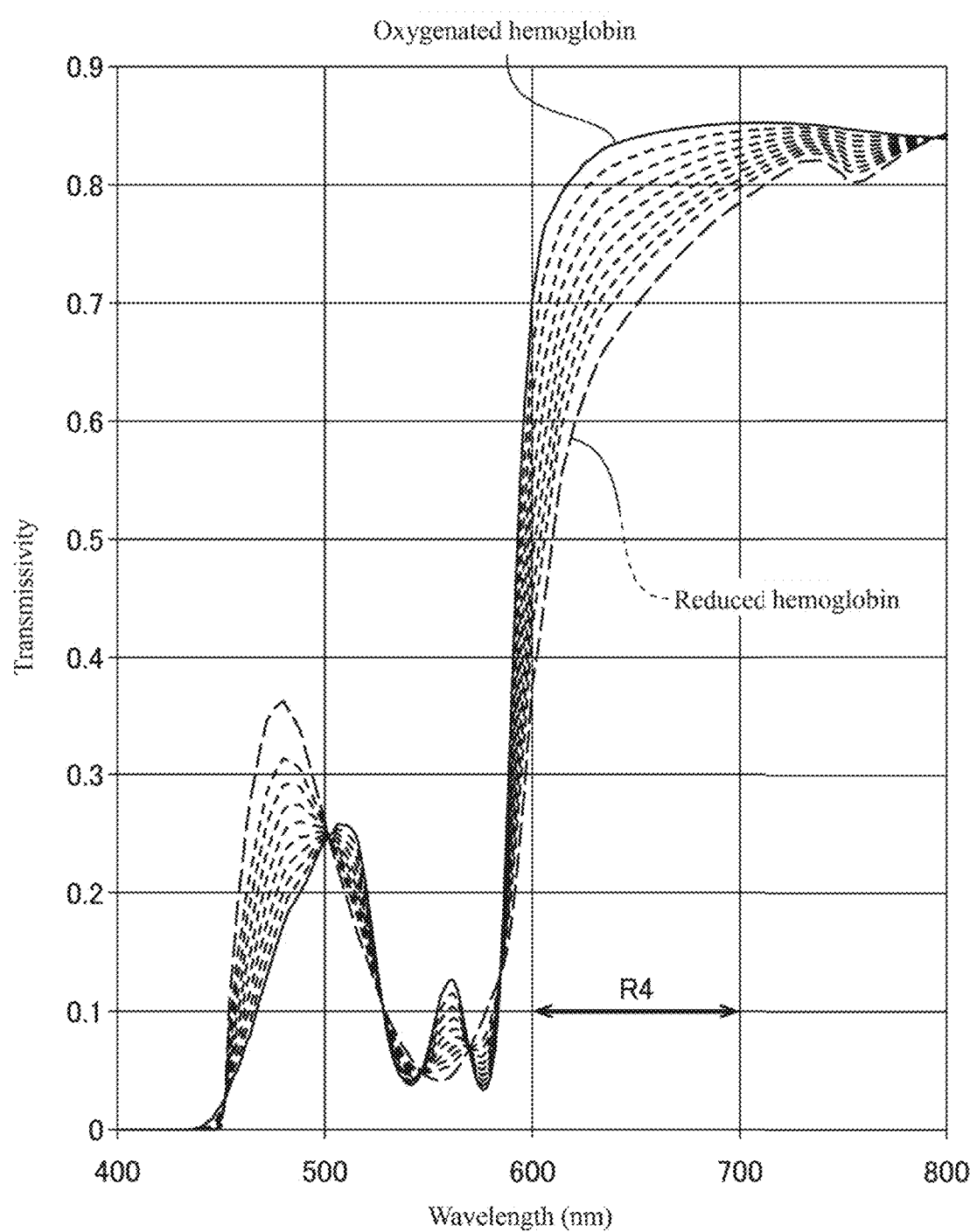
FIG. 1 shows the transmission spectrum of hemoglobin.
Figure 2:
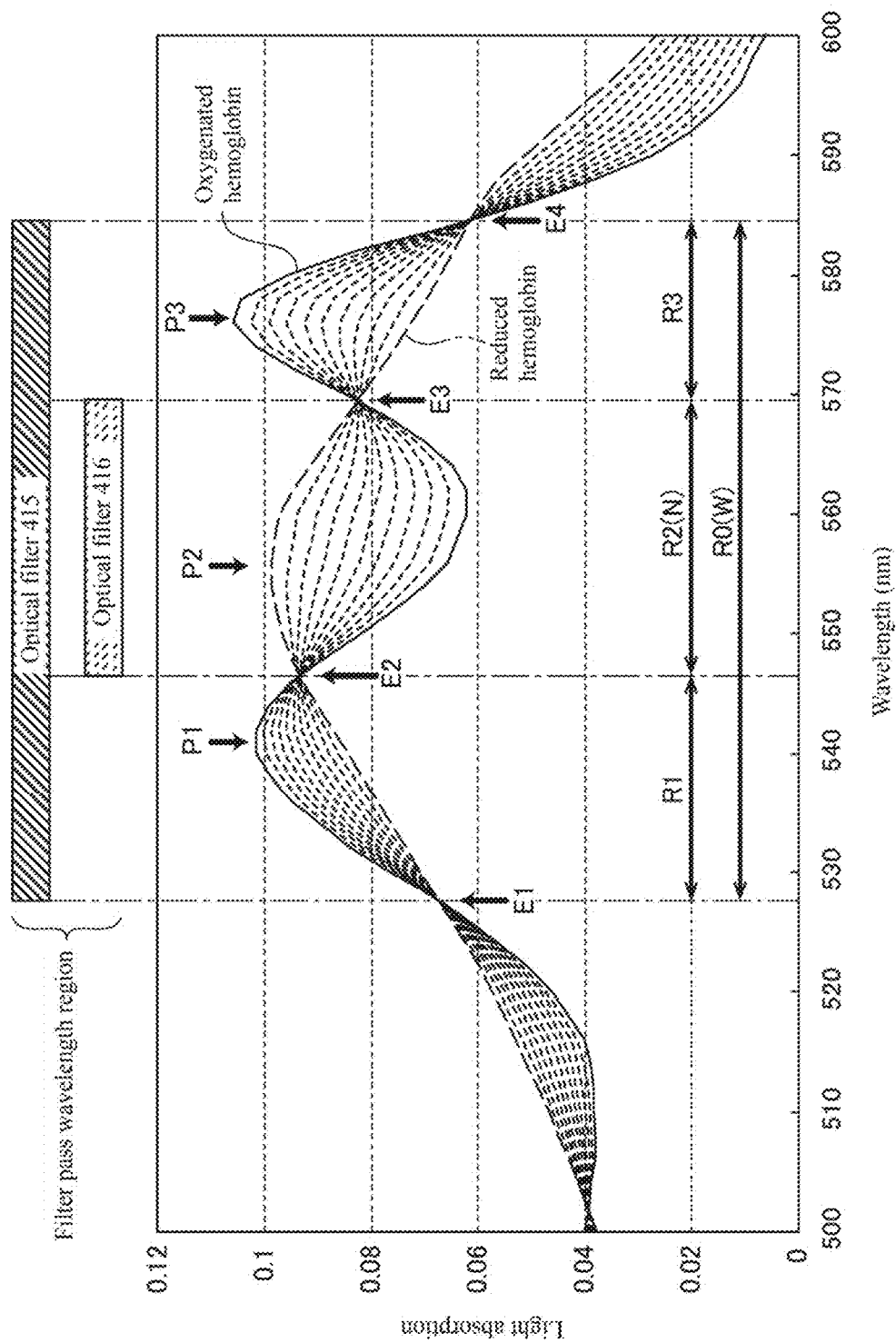
FIG. 2 shows the absorption spectrum of hemoglobin in the 500 to 600 nm band.

FIG. 1 shows the transmission spectrum of hemoglobin. Also, FIG. 2 shows the absorption spectrum of hemoglobin at roughly 550 nm. Hemoglobin has a strong absorption band at roughly 550 nm. The absorption spectrum of hemoglobin varies according to the degree of oxygen saturation (the percentage of oxygenated hemoglobin HbO in the total amount of hemoglobin). The solid line in FIGS. 1 and 2 indicates the spectrum in the case where the degree of oxygen saturation is 100% (i.e., the spectrum of oxygenated hemoglobin HbO), and the long dashed line indicates the case where the degree of oxygen saturation is 0% (i.e., the spectrum of reduced hemoglobin Hb). Also, the short dashed lines indicate the spectrums of hemoglobin (mixture of oxygenated hemoglobin HbO and reduced hemoglobin Hb) at intermediate degrees of oxygen saturation (10, 20, 30, . . . 90%).

As shown in FIG. 2, in the 500 to 600 nm band, oxygenated hemoglobin HbO and reduced hemoglobin Hb have mutually different peak wavelengths. Specifically, oxygenated hemoglobin HbO has an absorption peak P1 at a wavelength of roughly 542 nm (e.g., 542±5 nm) and an absorption peak P3 at a wavelength of roughly 576 nm (e.g., 576±5 nm). On the other hand, reduced hemoglobin Hb has an absorption peak P2 at roughly 556 nm (e.g., 556±5 nm). FIG. 2 shows a two-component absorption spectrum in which the sum of the concentrations of the respective components (oxygenated hemoglobin HbO and reduced hemoglobin Hb) is constant, and therefore isosbestic points E1 (roughly 528 nm [e.g., 528±5 nm]), E2 (roughly 547 nm [e.g., 547±5 nm]). E3 (roughly 569 nm [e.g., 569±5 nm]), and E4 (roughly 584 nm [e.g., 584±5 nm]), at which the absorption is constant regardless of the concentrations of the respective components (i.e., the degree of oxygen saturation), appear in the spectrum. In the following description, the wavelength region sandwiched between the isosbestic points E1 and E2 will be called a wavelength region R1, the wavelength region sandwiched between the isosbestic points E2 and E3 will be called a wavelength region R2, and the wavelength region sandwiched between the isosbestic points E3 and E4 will be called a wavelength region R3. Also, the wavelength region sandwiched between the isosbestic points E1 and E4 (i.e., the combination of the wavelength regions R1. R2, and R3) will be called a wavelength region R0. Also, in the following description, the wavelength region R2 is also called the N band (Narrow-band), and the wavelength region R0 is also called the W band (Wide-band).

As shown in FIG. 2, between adjacent isosbestic points, absorption by hemoglobin increases or decreases linearly relative to the degree of oxygen saturation. Also, in the regions between adjacent isosbestic points, absorption by hemoglobin changes roughly linearly relative to the degree of oxygen saturation.

Specifically, absorptions $A_{R1}$ and $A_{R3}$ of hemoglobin in the wavelength regions R1 and R3 linearly increase relative to the concentration of oxygenated hemoglobin. Also, an absorption $A_{R2}$ of hemoglobin in the wavelength region R2 linearly increases relative to the concentration of reduced hemoglobin.

Here, the degree of oxygen saturation is defined by Expression 1 below.

$$Sat = \frac{[HbO]}{[Hb] + [HbO]} \qquad \text{Expression 1}$$

where
Sat: degree of oxygen saturation
[Hb]: concentration of reduced hemoglobin
[HbO]: concentration of oxygenated hemoglobin
[Hb]+[HbO]: total hemoglobin concentration (tHb)

Also, Expression 2 and Expression 3 that express the concentrations of oxygenated hemoglobin and reduced hemoglobin are obtained from Expression 1.

$$[HbO]=Sat \cdot ([Hb]+[HbO]) \qquad \text{Expression 2}$$

$$[Hb]=(1-Sat) \cdot ([Hb]+[HbO]) \qquad \text{Expression 3}$$

Accordingly, the absorptions $A_{R1}$, $A_{R2}$, and $A_{R3}$ of hemoglobin are characteristic values that are dependent on both the degree of oxygen saturation Sat and the total hemoglobin concentration tHb.

Also, through research carried by the inventors of the present invention, it was found that an integrated value $A_{R0}$ of the absorption of hemoglobin in the wavelength region R0, which is made up of the wavelength regions R1, R2, and R3, is substantially a value that is not dependent on the degree of oxygen saturation Sat, but is determined by the total hemoglobin concentration tHb. Accordingly, the total hemoglobin concentration tHb can be determined based on the absorption $A_{R0}$.

Also, the degree of oxygen saturation Sat can be determined based on the total hemoglobin concentration tHb, which is determined based on the absorption $A_{R0}$, and the absorptions $A_{R1}$, $A_{R2}$, and $A_{R3}$. Note that as shown in FIG. 2, the amount of variation of the absorption according to the degree of oxygen saturation Sat in the wavelength regions R1, R2, and R3 (i.e., the area of the region enclosed by the solid-line waveform and the long-dash waveform), is the largest in the wavelength region R2, and the absorption $A_{R2}$ in the wavelength region R2 is the characteristic amount that is most sensitive to the degree of oxygen saturation Sat.

Also, the spectral characteristics of biological tissue are influenced by the scattering of light by the biological tissue. Specifically light scattering by biological tissue is a cause of error in the determination of the total hemoglobin concentration tHb and the degree of oxygen saturation Sat. In order to make an accurate determination based on image information regarding biological tissue, it is necessary to correct the influence of scattering.

A research group of the inventors of the present invention conducted research regarding indicators of the total hemoglobin concentration tHb and the degree of oxygen saturation Sat that can be acquired from image information regarding biological tissue, and found the three parameters W/R. W/(R+G), and N/W that are not dependent on light scattering in Expressions 4 to 6 below. The parameters W/R and W/(R+G) are parameters that are based on the quantitative relationship between the above-described absorption $A_{R0}$ and the total hemoglobin concentration tHb, and serve as an indicator of the total hemoglobin concentration tHb. Also, the parameter N/W is based on the quantitative relationship between the above-described absorption $A_{R2}$ and the degree of oxygen saturation Sat, and serves as an indicator of the degree of oxygen saturation Sat.

$$\frac{W}{R}(x, y) = \frac{W(x, y)}{R(x, y)} \quad \text{Expression 4}$$

$$\frac{W}{R+G}(x, y) = \frac{W(x, y)}{R(x, y) + G(x, y)} \quad \text{Expression 5}$$

$$\frac{N}{W}(x, y) = \frac{N(x, y)}{W(x, y)} \quad \text{Expression 6}$$

Here, W(x,y) is the value of the pixel (x,y) in image data acquired under illumination by light in the W band, and N(x,y) is the value of the pixel (x,y) in image data acquired under illumination by light in the N band. Note that the W band and the N band are included in the pass wavelength region of the G color filter of the single-CCD primary color image sensor. In other words, images formed by light in the W band and the N band are captured by the color pixels provided with the G color filter, and are obtained as G digital color image data.

Also, R(x,y) and G(x,y) are the values of the pixel (x,y) in image data acquired under illumination by white light. Specifically R(x,y) is the value of R digital color image data acquired by a color pixel provided with the R color filter, and G(x,y) is the value of G digital color image data acquired by a color pixel provided with the G color filter.

The parameters W/R and W/(R+G) have sensitivity to the total hemoglobin concentration tHb, but have almost no sensitivity to the degree of scattering and the degree of oxygen saturation Sat. For this reason, the parameters W/R and W/(R+G) can be used to acquire a value of the total hemoglobin concentration tHb that includes almost no error arising from the degree of scattering or the degree of oxygen saturation Sat.

Also, the parameter N/W has sensitivity to the total hemoglobin concentration tHb and the degree of oxygen saturation Sat, but has almost no sensitivity to the degree of scattering. For this reason, if the total hemoglobin concentration tHb is known, the parameter N/W can be used to obtain a value of the degree of oxygen saturation Sat that has almost no error arising from scattering.

Calculation Using Absorption in 600 to 700 nm Band

Also, as shown in FIG. 1, the tail of the 500 to 600 nm absorption band extends to the vicinity of 800 nm. In the 600 to 700 nm band (called the "wavelength region R4" hereinafter), absorption by hemoglobin linearly decreases monotonically relative to the degree of oxygen saturation Sat. The absorption $A_{R4}$ in the wavelength region R4 (particularly in the 600 to 650 nm band) is smaller than in the 500 to 600 nm band, but has a larger variation range relative to change in the degree of oxygen saturation Sat (i.e., is highly sensitive to the degree of oxygen saturation Sat), and thus can serve as an indicator of the degree of oxygen saturation Sat.

Although it is difficult to precisely calculate the absorption $A_{R4}$, from biological tissue image data, the parameters R/(R+G+B) and R/W found by the inventors of the present invention serve as indicators that indicate the absorption $A_{R4}$ and are correlated with the degree of oxygen saturation (Expressions 7 and 8). By using the parameter R/(R+G+B) or R/W, it is possible to easily calculate an indicator that indicates the absorption $A_{R4}$ (and the degree of oxygen saturation Sat) based on biological tissue image data.

$$\frac{R}{R+G+B}(x, y) = \frac{R(x, y)}{R(x, y) + G(x, y) + B(x, y)} \quad \text{Expression 7}$$

$$\frac{R}{W}(x, y) = \frac{R(x, y)}{W(x, y)} \quad \text{Expression 8}$$

In Expression 7, B(x,y) is the value of the pixel (x,y) in the image data acquired under illumination by white light. Specifically. B(x,y) is the value of B digital color image data acquired by a color pixel provided with the B color filter.

The absorption $A_{R4}$ is dependent on the total hemoglobin concentration tHb. Accordingly, the parameters R/(R+G+B) and R/W that are indicators of the absorption $A_{R4}$ are also dependent on the total hemoglobin tHb. In order to obtain an accurate degree of oxygen saturation Sat, the parameters R/(R+G+B) and R/W need to be corrected for the influence of the total hemoglobin concentration tHb.

Next, a method for correcting error arising from the total hemoglobin concentration tHb will be described taking the example of the parameter R/(R+G+B).

Figure 3:
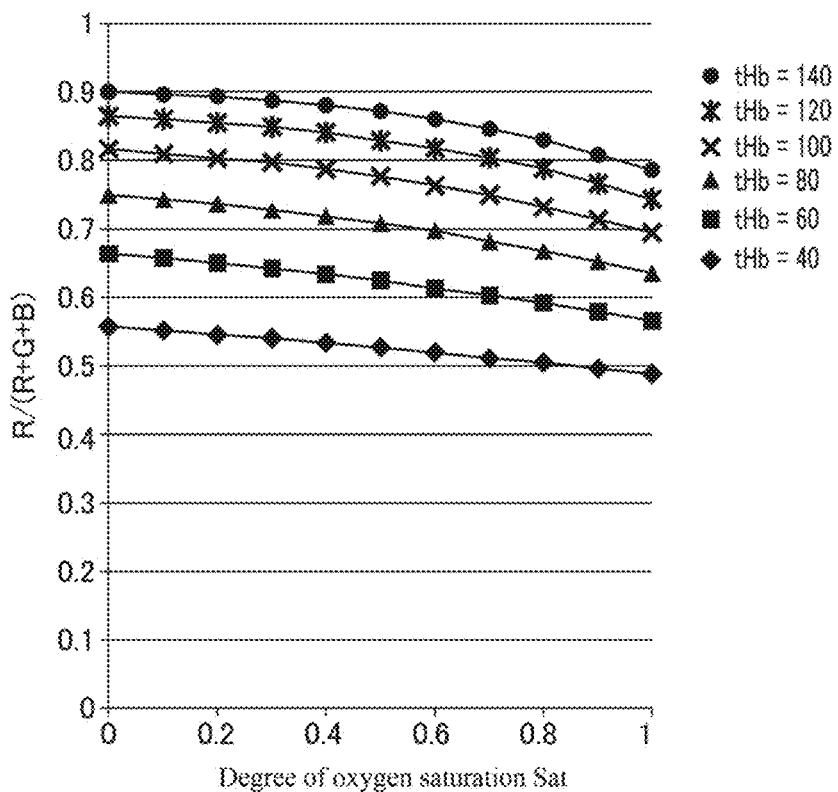
FIG. 3 is a graph showing the relationship between the degree of oxygen saturation and a parameter R/(R+G+B).

FIG. 3 is a graph plotting the relationship between the degree of oxygen saturation Sat and the parameter R/(R+G+B). Even in the case where the degree of oxygen saturation Sat has the same value, the value of the parameter R/(R+G+B) increases according to an increase in the total hemoglobin concentration tHb, and an accurate degree of oxygen saturation Sat cannot be obtained based on only the parameter R/(R+G+B).

Figure 4:
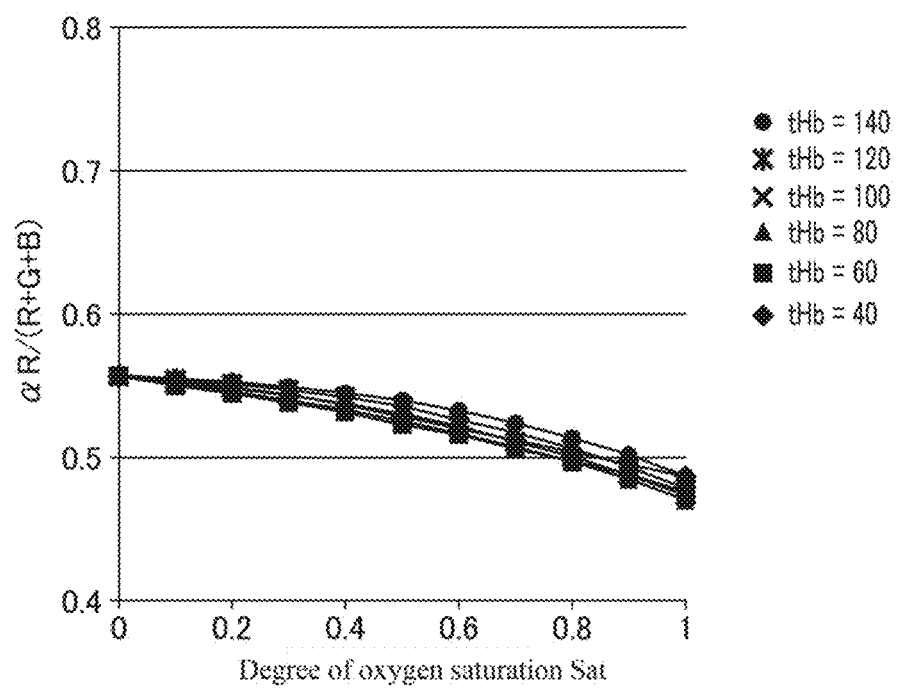
FIG. 4 is a graph showing the relationship between the degree of oxygen saturation and a parameter $\alpha$R/(R+G+B).

FIG. 4 is a graph plotting a parameter αR/(R+G(+B), which is obtained by multiplying the parameter R/(R+G+B) by a correction value α(tHb) determined by the total hemoglobin concentration tHb, relative to the degree of oxygen saturation Sat. In FIG. 4, the values in all of the total hemoglobin concentrations tHb are distributed on approximately the same curve, and the parameter αR/(R+G+B) takes a value that has almost no dependency on the total hemoglobin concentration tHb.

The value of the correction value α(tHb) is obtained by the value of the parameter R/(R+G+B) under a predetermined reference condition (e.g., Sat=0 and tHb=40) being divided by the value of the parameter R(R+G+B) at each total hemoglobin concentration tHb with the same degree of oxygen saturation Sat as the reference condition (Sat=0 in this example).

Although it is difficult to precisely calculate the value of the total hemoglobin concentration tHb from biological tissue image data, the parameter R/G found by the inventors of the present invention serves as an indicator that indicates the total hemoglobin concentration tHb (Expression 9). By using the parameter R/G, it is possible to easily calculate an indicator that indicates the total hemoglobin concentration tHb based on biological tissue image data.

$$\frac{R}{G}(x, y) = \frac{R(x, y)}{G(x, y)} \quad \text{Expression 9}$$

Figure 5:
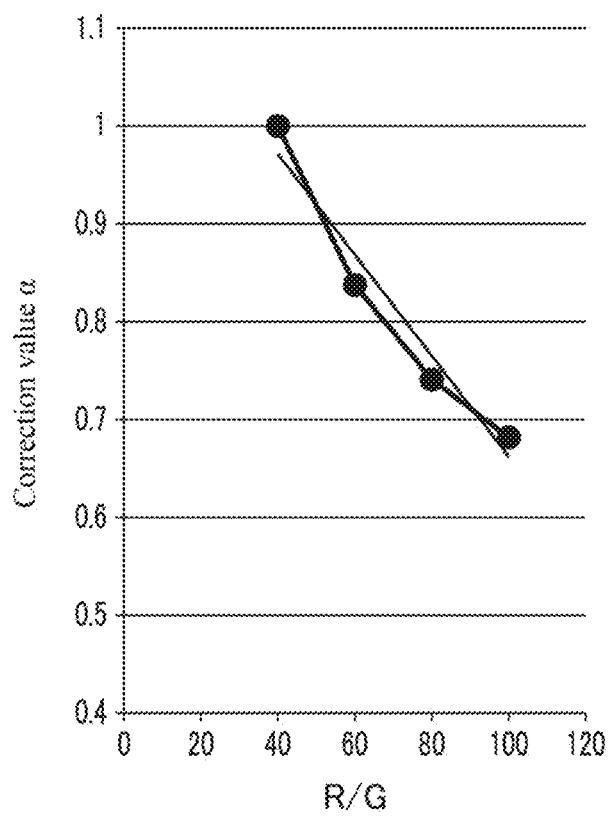
FIG. 5 is a graph showing the relationship between a parameter R/G and a correction value $\alpha$.

FIG. 5 is a graph plotting the relationship between the parameter R/G and the correction value α acquired experimentally. With use of this graph, the value of the correction value α can be obtained from the value of the parameter R/G.

Absorption is high in the 500 to 600 nm band (wavelength regions R1 to R3), and therefore the parameters of Expression 1 to 6, which make use of absorption in the wavelength regions R1 to R3 (particularly the parameter N/W of Expression 6 that makes use of the image data N acquired under illumination by light in the wavelength region R2 that is a narrow wavelength region and has a low light quantity) are suited to the evaluation of biological tissue that has a relatively low total hemoglobin concentration tHb.

On the other hand, absorption is low in the 600 to 700 nm band (wavelength region R4), and therefore the parameters of Expressions 7 to 9, which make use of absorption in the wavelength region R4, are suited to the evaluation of biological tissue that has a relatively high total hemoglobin concentration tHb.

In the embodiment of the present invention described below, in the case of biological tissue that has a relatively low total hemoglobin concentration tHb, the concentration of a biological substance in the biological tissue (specifically the total hemoglobin concentration tHb and the degree of oxygen saturation Sat) is calculated based on intense absorption in the wavelength regions R1 to R3, and in the case of biological tissue that has a relatively high total hemoglobin concentration tHb, the concentration of a biological substance in the biological tissue is calculated based on weak absorption in the wavelength region R4. In this way, by using a configuration in which the wavelength region used in calculation of the degree of oxygen saturation Sat is selected according to the magnitude of the total hemoglobin concentration tHb, it is possible to acquire an accurate degree of oxygen saturation Sat over a wide concentration range.

Configuration of Endoscope Apparatus

Figure 6:
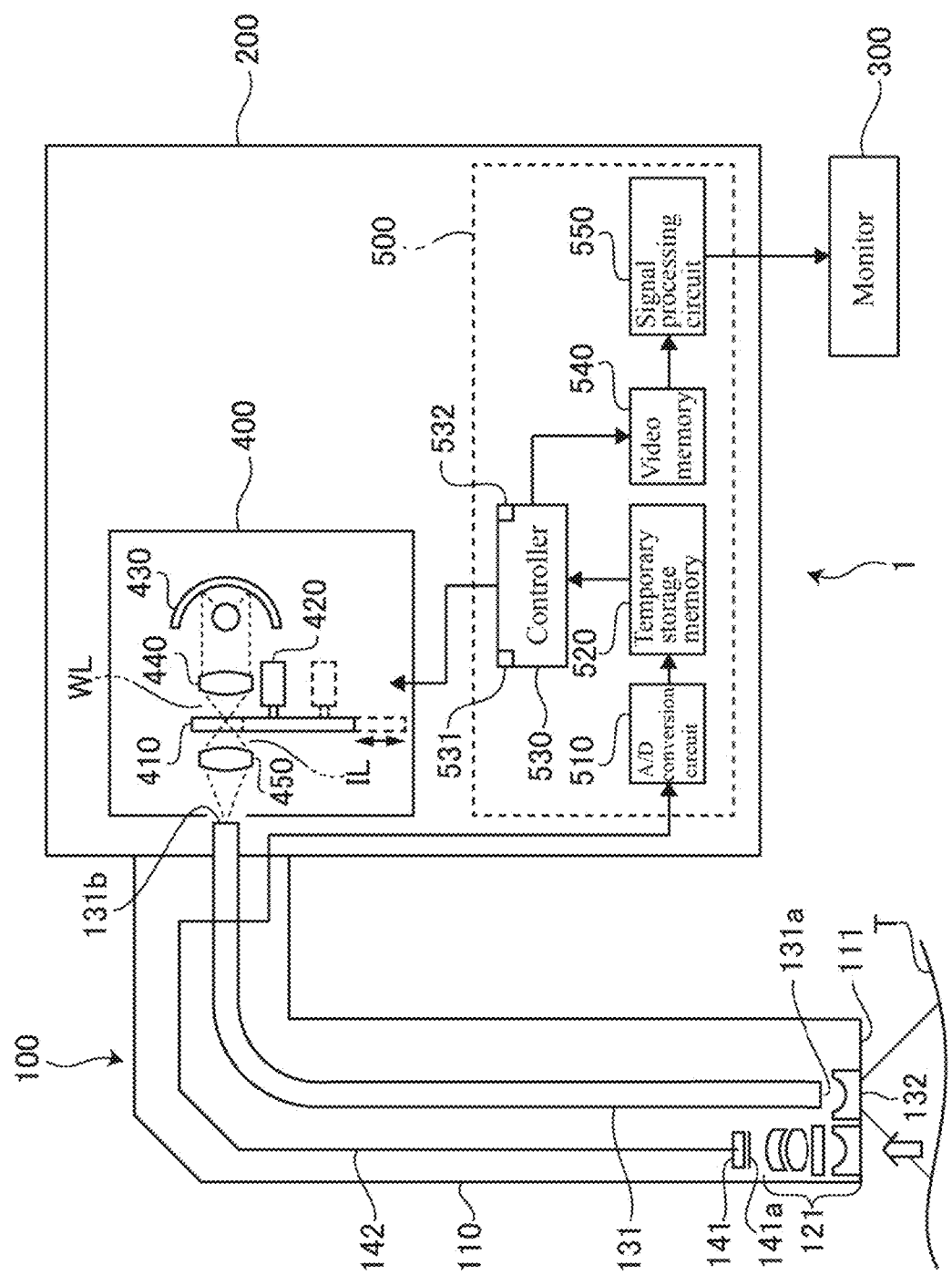
FIG. 6 is a block diagram of an endoscope apparatus according to an embodiment of the present invention.

FIG. 6 is a block diagram of an endoscope apparatus 1 according to this embodiment of the present invention. The endoscope apparatus 1 of the present embodiment includes an electronic endoscope 100, a processor 200, and a monitor 300. The electronic endoscope 100 and the monitor 300 are detachably connected to the processor 200. Also, a light source unit 400 and an image processing unit 500 are built into the processor 200.

The electronic endoscope 100 has an insertion tube 110 for insertion into the subject's body. The electronic endoscope 100 is internally provided with a light guide 131 that extends over approximately the entire length thereof. One end portion (distal end portion 131a) of the light guide 131 is arranged in the distal end portion of the insertion tube 110 (insertion tube distal end portion 111), and the other end portion (base end portion 131b) of the light guide 131 is connected to the processor 200. The processor 200 includes a light source unit 400 that is one example of a white light source and includes a light source lamp 430 or the like for generating high-intensity white light WL, such as a xenon lamp, and the illumination light IL generated by the light source unit 400 enters the base end 131b of the light guide 131. Light that enters the base end 131b of the light guide 131 passes through the light guide 131 and is guided to the distal end portion 131a thereof, and is then emitted from the distal end portion 131a. A light distribution lens 132 arranged opposing the distal end portion 131a of the light guide 131 is provided at the insertion tube distal end portion 111 of the electronic endoscope 100, and illumination light IL emitted from the distal end portion 131a of the light guide 131 passes through the light distribution lens 132 and illuminates biological tissue T in the vicinity of the insertion tube distal end portion 111.

Also, the insertion tube distal end portion 111 is provided with an objective optical system 121 and an image sensor 141 that is one example of an imaging unit. Part of the illumination light IL reflected or scattered by the surface of the biological tissue T (returning light) enters the objective optical system 121, is condensed, and forms an image on the light receiving surface of the image sensor 141. The image sensor 141 of the present embodiment is a CCD (Charge Coupled Device) image sensor for color image capturing, and includes a color filter 141a on its light receiving surface. Another type of image sensor such as a CMOS (Complementary Metal Oxide Semiconductor) image sensor may be used as the image sensor 141.

Figure 7:
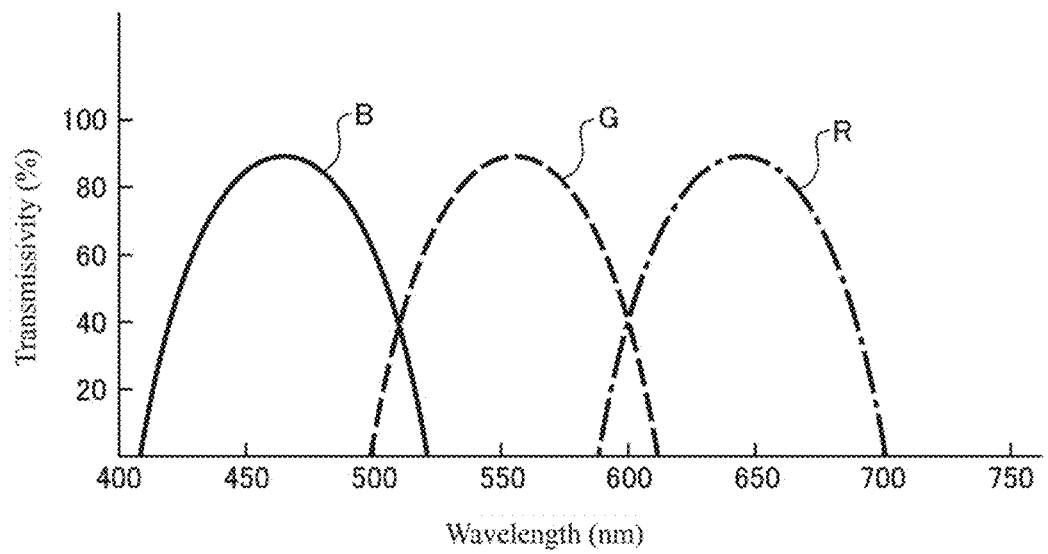
FIG. 7 shows the transmission spectrum of color filters included in an image sensor.

The color filter 141a includes an array of R color filters that allow red light to pass, G color filters that allow green light to pass, and B color filters that allow blue light to pass, and is a so-called on-chip filter that is formed directly on the light receiving element of the image sensor 141. The R, G, and B filters have the spectral characteristics shown in FIG. 7. In other words, the R color filters of the present embodiment are filters that allow light with a wavelength longer than approximately 570 nm to pass, the G color filters are filters that allow light with a wavelength of approximately 500 nm to 620 nm to pass, and the B color filters are filters that allow light with a wavelength shorter than approximately 530 nm to pass.

The image sensor 141 is controlled to operate in synchronization with a signal processing circuit 550 that will be described later, and periodically (e.g., at intervals of 1/30 second) outputs an imaging signal that corresponds to a subject image formed on the light receiving surface. The imaging signal output from the image sensor 141 is sent to the image processing unit 500 of the processor 200 via a cable 142.

The image processing unit 500 includes an A/D conversion circuit 510, a temporary storage memory 520, a controller 530, a video memory 540, and a signal processing circuit 550. The A/D conversion circuit 510 performs A/D conversion on an imaging signal received from the image sensor 141 of the electronic endoscope 100 via the cable 142, and outputs digital image data. The digital image data output from the A/D conversion circuit 510 is sent to and stored in the temporary storage memory 520. This digital image data includes R digital image data obtained by the light receiving elements on which the R color filters are mounted, G digital image data obtained by the light receiving elements on which the G color filters are mounted, and B digital image data obtained by the light receiving elements on which the B color filters are mounted. Note that in the present specification, the R digital image data, the G digital image data, and the B digital image data will also be called single-color image data (R single-color image data. (3 single-color image data, and B single-color image data).

The controller 530 processes one or more pieces of digital image data stored in the temporary storage memory 520 to generate screen data for display on the monitor 300, and sends the screen data to the video memory 540. For example, the controller 530 generates screen data based on one piece of digital image data, screen data in which multiple pieces of digital image data are arranged side-by-side, screen data that includes an image that shows healthy sites and lesion sites in different colors based on a reflection spectrum for the biological tissue T generated for each pixel (x,y) based on multiple pieces of digital image data, or screen data that displays a graph of the reflection spectrum of the biological tissue T that corresponds to a certain pixel (x,y), and then stores the screen data in the video memory 540. The signal processing circuit 550 generates a video signal in a predetermined format (e.g., a format compliant with NTSC standards or DVI standards) based on screen data that is stored in the video memory 540, and outputs the video signal. The video signal output from the signal processing circuit 550 is received by the monitor 300. As a result, an endoscopic image or the like captured by the electronic endoscope 100 is then displayed on the monitor 300.

In this way, the processor 200 includes both functionality as a video processor that processes imaging signals output from the image sensor 141 of the electronic endoscope 100, and functionality as a light source apparatus that supplies illumination light IL, which is for illuminating biological tissue T that is the imaging subject, to the light guide 131 of the electronic endoscope 100.

Besides the above-described light source 430, the light source unit 400, which is one example of a light source apparatus, also includes a condensing lens 440, a rotating filter 410, a filter control unit 420, and a condensing lens 4150. Approximately parallel white light WL that exits the light source 430 is condensed by the condensing lens 440, passes through the rotating filter 410, is then again condensed by the condensing lens 450, and then enters the base end 131b of the light guide 131. Note that the rotating filter 410 can be moved between an application position on the optical path of the white light WL and a retracted position off the optical path by a moving means (not shown) such as a linear guideway.

Note that the configuration of the light source unit 400 is not limited to the configuration shown in FIG. 6. For example, a lamp that generates convergent light may be employed as the light source 430. In this case, a configuration may be employed in which, for example, white light WL is condensed before reaching the condensing lens 440, and then caused to enter the condensing lens 440 as diffused light.

Also, a configuration may be employed in which the condensing lens 440 is not used, and approximately parallel light generated by the light source 430 is caused to directly enter the rotating filter 410.

Also, in the case of using a lamp that generates convergent light, a configuration may be employed in which a collimator lens is used instead of the condensing lens 440 in order to cause white light WL that is in an approximately parallel state to enter the rotating filter 410. For example, in the case of using an interference type of optical filter such as a dielectric multilayer filter as the rotating filter 410, by causing approximately parallel white light. WL to enter the rotating filter 410, the angle of incidence of the white light WL on the optical filter can be made uniform, thus making it possible to obtain more favorable filter characteristics.

Also, a lamp that generates diverging light may be applied as the light source 430. In this case as well, a configuration can be employed in which a collimator lens is used instead of the condensing lens 440 in order to cause approximately parallel white light WL to enter the rotating filter 410.

The rotating filter 410 is a disc-type optical unit that includes multiple optical filters, and is configured such that the pass wavelength region is switched according to the rotation angle. The rotation angle of the rotating filter 410 is controlled by the filter control unit 420, which is connected to the controller 530. The controller 530 controls the rotation angle of the rotating filter 410 via the filter control unit 420, thus switching the spectrum of illumination light IL that passes through the rotating filter 410 and is supplied to the light guide 131.

Figure 8:
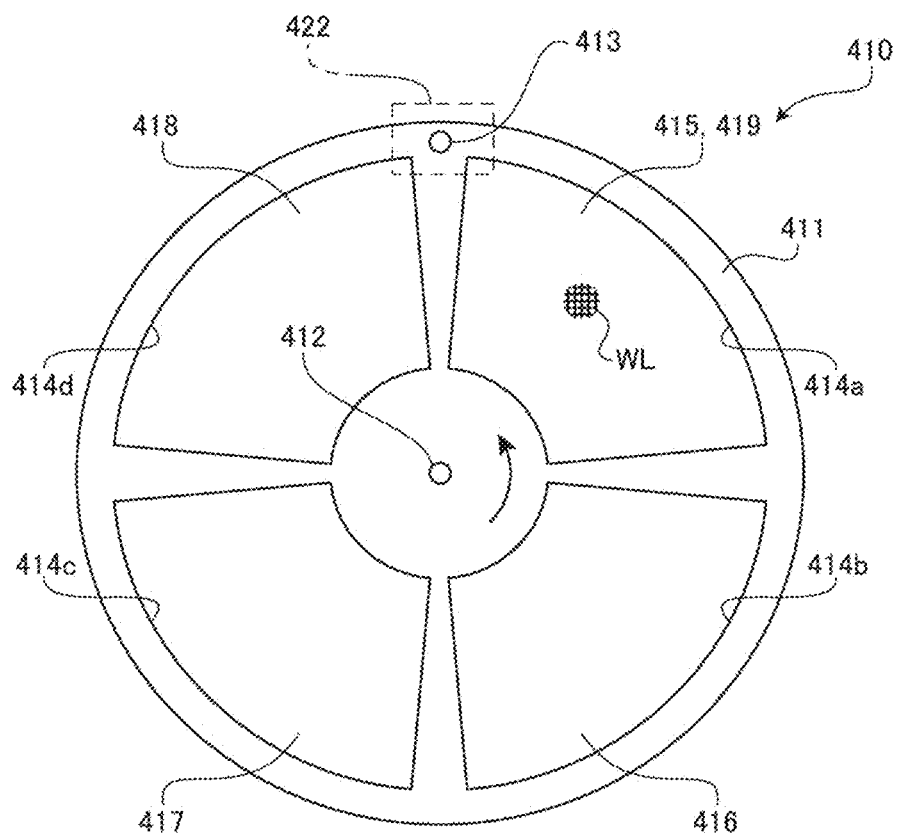
FIG. 8 is an external view of a rotating filter.

FIG. 8 is an external view (front view) of the rotating filter 410. The rotating filter 410 includes an approximately disc-shaped frame 411 and three fan-shaped optical filters 415, 416, and 418. The optical filters 415 and 416 are examples of a first optical filter and a second optical filter respectively. Three fan-shaped windows 414a, 414b, and 414c are formed with equal gaps therebetween around the central axis of the frame 411, and the optical filters 415, 416, and 418 are respectively fitted into the windows 414a. 414b, and 414e. Note that the optical filters of the present embodiment are all dielectric multilayer filters, but another type of optical filter (e.g., an absorption optical filter or an etalon filter that uses a dielectric multilayer film as a reflection film) may be used.

Also, a boss hole 412 is formed on the central axis of the frame 411. An output shaft of a servo motor (not shown) of the filter control unit 420 is inserted in and fixed to the boss hole 412, and the rotating filter 410 rotates along with the output shaft of the servo motor.

Although the state where white light WL enters the optical filter 415 is shown in FIG. 8, when the rotating filter 410 rotates in the direction indicated by the arrow, the optical filter that the white light WL enters successively switches between the optical filters 415, 416, and 418 in this order, and thus the spectrum of illumination light IL that passes through the rotating filter 410 switches successively.

The optical filters 415 and 416 are optical bandpass filters that selectively allow light in the 550 nm band to pass. As shown in FIG. 2, the optical filter 415 is configured to allow light in the wavelength region from the isosbestic points E1 to E4 (i.e., the wavelength region R0 (W band)) to pass with low loss, and block light in other wavelength regions. Also, the optical filter 416 is configured to allow light in the wavelength region from the isosbestic points E2 to E3 (i.e., the wavelength region R2 (N band)) to pass with low loss, and block light in other wavelength regions.

As shown in FIG. 2, the wavelength region R1 includes the peak wavelength of the absorption peak P1 derived from oxygenated hemoglobin, the wavelength region R2 includes the peak wavelength of the absorption peak P2 derived from reduced hemoglobin, and the wavelength region R3 includes the peak wavelength of the absorption peak P3 derived from oxygenated hemoglobin. Also, the wavelength region R0 includes the peak wavelengths of the three absorption peaks P1, P2, and P3.

Also, the W band and the N band, which are the pass wavelength regions of the optical filters 415 and 416 (FIG. 2), are included in the pass wavelength region of the G color filter of the color filter 141a. Accordingly, a subject image formed by light that passes through the optical filters 415 and 416 is captured by the light receiving elements on which the (color filters are mounted in the image sensor 141, and is obtained as G digital image data.

Also, the optical filter 418 is an ultraviolet cut filter, and illumination light IL that passes through the optical filter 418 (i.e., white light) is used in the capture of a normal observation image. Note that a configuration is possible in which the optical filter 418 is not used, and the window 414c of the frame 411 is open. Also, in the present specification, illumination light 1L that passes through the optical filters 415 and 416 is also called special light (or special observation light), and white light (or wide band light) that passes through the optical filter 418 is also called normal light (or normal observation light).

Also, a light attenuation filter (ND filter) 419 is attached over the optical filter 115 in the window 414a. The light attenuation filter 119 has no wavelength dependency over the entire visible light range, and merely reduces the quantity of light with no change in the spectrum of illumination light IL. By using the light attenuation filter 419, the quantity of illumination light IL that passes through the optical filter 415 and the light attenuation filter 419 is adjusted to approximately the same as the quantity of illumination light IL that passes through the optical filter 416. Accordingly, regardless of whether illumination light IL that passed through the optical filter 415 or the optical filter 416 is used, it is possible to capture an image with the same exposure time and appropriate exposure.

In the present embodiment, a fine metal mesh is used as the light attenuation filter 419. Besides a metal mesh, another type of light attenuation filter such as a slit or half mirror type may be used. Also, a configuration is possible in which a light attenuation filter is not used, and the transmissivities of the optical filters 415 and 416 themselves are adjusted. Also, a light attenuation filter may be attached to the windows 414b and 414c as well. Moreover, the passing light quantity may be adjusted by changing the central angles (i.e., opening areas) of the windows 414a to 414c. Furthermore, a configuration is possible in which a light attenuation filter is not used, and the exposure time is adjusted for each optical filter that is used.

A through-hole 413 is formed in the peripheral edge portion of the frame 411. The through-hole 413 is formed at the same position (phase) as the boundary portion between the window 414a and the window 414e in the rotation direction of the frame 411. A photo interrupter 422 for detecting the through-hole 413 is arranged in the periphery of the frame 411 so as to surround a portion of the peripheral edge portion of the frame 411. The photo interrupter 422 is connected to the filter control unit 420.

The endoscope apparatus 1 of the present embodiment has two operating modes, namely a normal observation mode and a spectral analysis mode. The normal observation mode is an operating mode for capturing color images using illumination light IL (normal light) that passed through the optical filter 418. The spectral analysis mode is a mode for performing spectral analysis based on digital image data obtained using illumination light IL (special light) that passed through the optical filters 415 and 416 respectively, and displaying a biomolecule distribution image of biological tissue (e.g., a degree of oxygen saturation distribution image). The operating mode of the endoscope apparatus 1 is switched by a user operation performed on an operation panel (not shown) of the processor 200 or an operation button (not shown) of the electronic endoscope 100, for example.

In the normal observation mode, the controller 530 controls the moving means to move the rotating filter 410 from the application position to the retracted position. Note that in the spectroscopic analysis mode, the rotating filter 410 is arranged at the application position. Also, in the case where the rotating filter 410 does not have a moving means, the controller 530 controls the filter control unit 420 to stop the rotating filter 410 at a position at which white light WL enters the optical filter 418. Then, digital image data obtained by the image sensor 141 is subjected to predetermined image processing such as demosaicing, and then converted into a video signal and displayed on the screen of the monitor 300.

In the spectral analysis mode, the controller 530 controls the filter control unit 420 to drive the rotating filter 410 to rotate at a constant rotational frequency and successively capture images of the biological tissue T using illumination light IL that passes through the optical filters 415, 416, and 418. An image that shows the distribution of biomolecules in the biological tissue is then generated based on digital image data obtained using illumination light IL that passed through the optical filters 415 and 416, and then a display screen that arranges the generated image and the normal observation image obtained using the optical filter 418 side-by-side is generated, converted into a video signal, and displayed on the monitor 300.

In the spectroscopic analysis mode, the filter control unit 420 detects the phase of rotation of the rotating filter 410 based on the timing of detection of the through-hole 413 by the photo interrupter 422, compares the detected phase with the phase of a timing signal supplied by the controller 530, and adjusts the phase of rotation of the rotating filter 410. The timing signal from the controller 530 is synchronized with the drive signal for the image sensor 141. Accordingly, the rotating filter 410 is driven to rotate at a substantially constant rotational frequency in synchronization with the driving of the image sensor 141. Specifically, the rotation of the rotating filter 410 is controlled such that the one of the optical filters 415, 416, and 418 (windows 414a-c) that white light WL enters is switched each time one image (three R, G, and B frames) is captured by the image sensor 141.

Figure 9:
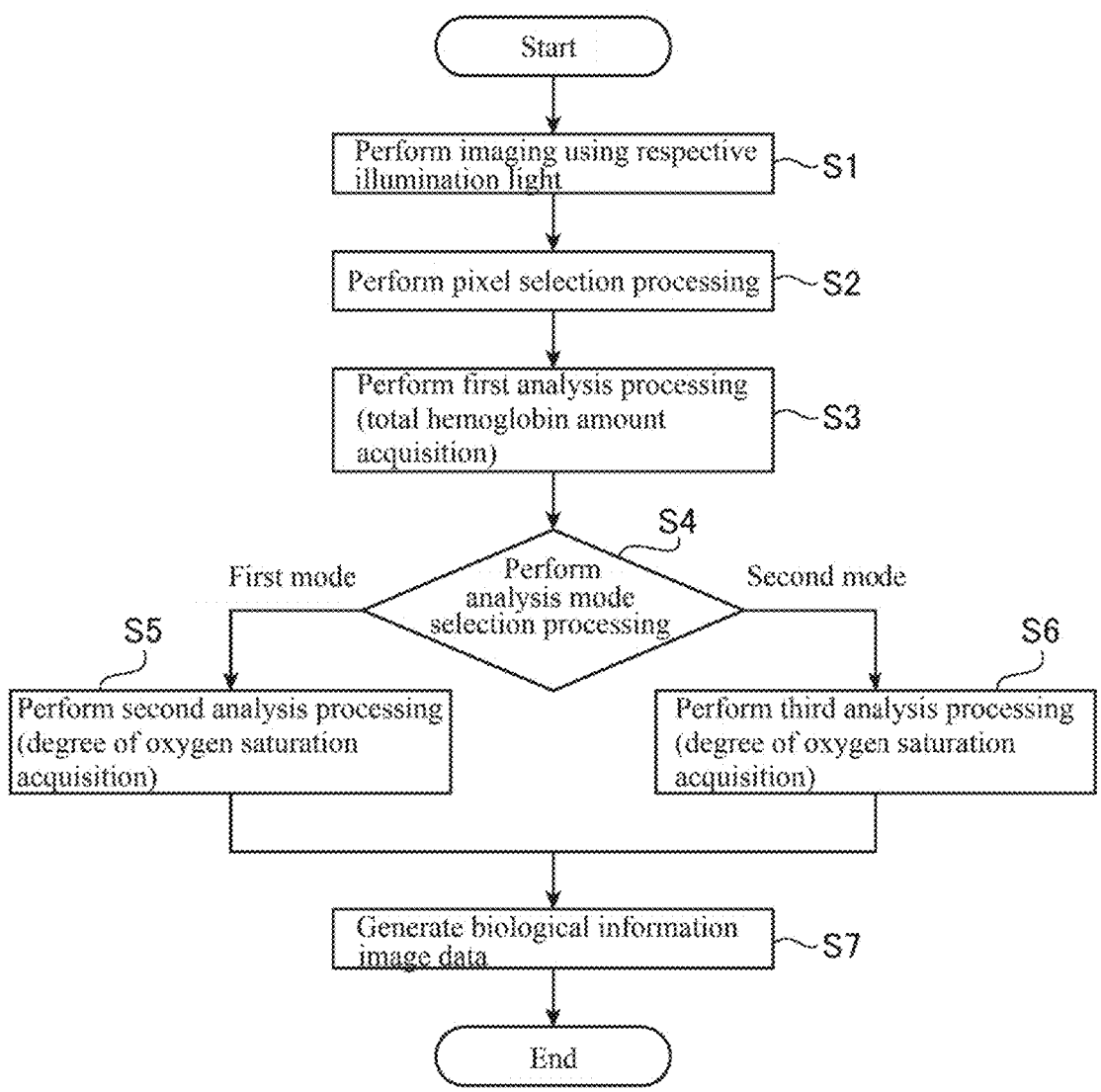
FIG. 9 is a flowchart showing spectral analysis processing according to the embodiment of the present invention.

Next, spectral analysis processing executed in the spectral analysis mode will be described. FIG. 9 is a flowchart showing a procedure of spectral analysis processing.

If the spectral analysis mode has been selected by a user operation, the filter control unit 420 drives the rotating filter 410 to rotate at a constant rotational frequency as described above. Illumination light IL is successively supplied from the light source unit 400, and then through the optical filters 415, 416, and 418, and images are successively captured using the respective types of illumination light IL (S1). Specifically. G digital image data W(x,y) obtained using illumination light IL that passes through the optical filter 415. G digital image data N(x,y) obtained using illumination light IL that passes through the optical filter 416, and R digital image data R(x,y). (G digital image data G (x,y), and B digital image data B (x,y) obtained using illumination light IL (white light) that passes through the optical filter (ultraviolet cut filter) 418 are stored in the internal memory 531 of the controller 530.

Next, the image processing unit 500 performs pixel selection processing S2 for selecting pixels that are to be subjected to subsequent analysis processing (processing S3-S7), using the R digital image data R (x,y), the (3 digital image data C (x,y), and the B digital image data B (x,y) acquired in processing S1. The image processing unit 500 is one example of a feature amount acquisition unit, that acquires a feature amount of biological tissue.

At locations where blood is not included, or locations where the biological tissue color is dominantly influenced by a substance other than hemoglobin, even if the degree of oxygen saturation or blood flow is calculated based on color information of the pixel, a meaningful value is not obtained, but rather is simply noise. If such noise is presented to a physician, it will not only be a hindrance to the physician's diagnosis, but also have the harmful effect of placing an unnecessary burden on the image processing unit 500 and reducing the processing speed. In view of this, the analysis processing of the present embodiment is configured such that pixels suited to analysis processing (i.e., pixels recording the spectroscopic features of hemoglobin) are selected, and analysis processing is performed on only the selected pixels.

In pixel selection processing S2, only pixels that satisfy all of the conditions of Expressions 10, 11, and 12 below are selected as target pixels for analysis processing.

$$B(x,y)/G(x,y) > a_1 \qquad \text{Expression 10}$$

$$R(x,y)/G(x,y) > a_2 \qquad \text{Expression 11}$$

$$R(x,y)/B(x,y) > a_3 \qquad \text{Expression 12}$$

Here, $a_1$, $a_2$, and $a_3$ are positive constants.

The above three conditional expressions are set based on the magnitude relationship of G component value<B component value<R component value in the transmission spectrum of blood. Note that pixel selection processing S2 may be performed using only one or two of the above three conditional expressions (e.g., using only Expressions 11 and 12 when focusing on the color red which is specific to blood).

Next, the image processing unit 500 performs first analysis processing S4. The non-volatile memory 532 of the controller 530 holds a numerical value table T1 (or function) that expresses the quantitative relationship between the parameter W/R and the total hemoglobin concentration tHb, a numerical value table T2 (or function) that expresses the relationship between the total hemoglobin concentration tHb, the parameter N/W, and the degree of oxygen saturation Sat, a numerical value table T3 (or function) that expresses the relationship between the parameter R/G and the correction value α, and a numerical value table T4 (or function) that expresses the relationship between the parameter αR/(R+G+B) and the degree of oxygen saturation Sat. The non-volatile memory 532 is an example of first to third storage units. In the first analysis processing S3, this numerical value table T1 is used to acquire the value of the total hemoglobin concentration tHb based on the G digital image data W(x,y) and the R digital image data R(x,y) acquired in processing S1.

Specifically, first, the parameter W/R(x,y) for each pixel (x,y) is calculated using Expression 13.

$$W/R(x,y)=W(x,y)/R(x,y) \qquad \text{Expression 13}$$

Next, the numerical value table T1 is referenced to read out and acquire the value of the total hemoglobin concentration tHb(x,y) that corresponds to the value of the parameter W/R(x,y) calculated using Expression 13.

The quantitative relationship in the numerical value table T1 (and the later-described numerical value tables T2, T3, and T4) held in the non-volatile memory 532 is obtained in advance by theoretical calculation or experimentation.

Next, the image processing unit 500 performs analysis mode selection processing S4. The spectral analysis mode includes a first spectral analysis mode (called the "first mode" hereinafter) in which the degree of oxygen saturation Sat is acquired based on absorption in the 550 nm band (wavelength region R0) and a second spectral analysis mode (called the "second mode" hereinafter) in which the degree of oxygen saturation Sat is acquired based on absorption in the 650 nm band (wavelength region R4). The first spectral analysis mode that uses the 550 nm band, in which absorption by hemoglobin is high, is suited to the case of analyzing biological tissue that contains a relatively small amount of blood. The second spectral analysis mode that uses the 650 nm band, in which absorption by hemoglobin is not very high, and in which sensitivity to the degree of oxygen saturation is high, is suited to the case of analyzing biological tissue that contains a relatively large amount of blood. In analysis mode selection processing S4, a parameter that has a correlation with the amount of blood contained in biological tissue (total hemoglobin concentration) is calculated, and the first spectral analysis mode or the second spectral analysis mode is selected for application based on the parameter.

In analysis mode selection processing S4 of the present embodiment, in the case of a pixel (x,y) that satisfies the condition of Expression 14, it is determined that the pixel corresponds to an image of biological tissue that contains a relatively small amount of blood, and the first mode is selected. Also, in the case of a pixel (x,y) that does not satisfy the condition of Expression 14, it is determined that the pixel corresponds to an image of biological tissue that contains a relatively large amount of blood, and the second mode is selected.

$$R(x,y)/G(x,y)>a_4 \qquad \text{Expression 14}$$

Here, $a_4$ is a positive constant.

Also, instead of Expression 14 above, a configuration is possible in which the conditional expression shown in Expression 15 is used, the first mode is selected when this conditional expression is satisfied, and the second mode is selected when this conditional expression is not satisfied.

$$R(x,y)/W(x,y)>a_5 \qquad \text{Expression 15}$$

Here, $a_5$ is a positive constant.

Note that the conditional expression used in analysis mode selection processing S4 is not limited to Expression 14 or 15. Another parameter that has a correlation with the amount of blood contained in biological tissue may be used.

The boundary condition (constant $a_4$ or $a_5$) in analysis mode selection processing S4 is set such that the extent of error in the analysis results of the first mode and the second mode is the same (i.e., the spectral analysis mode that obtains less error is selected), for example.

Also, the higher the amount of blood contained is, and the higher the absorption by hemoglobin is, the more difficult it is for illumination light IL to reach a deep portion of the biological tissue, and therefore the influence of scattering by the biological tissue decreases. In view of this, a configuration is possible in which the second mode is selected if error arising from scattering is sufficiently small. In this case, even if correction for scattering is omitted in the second mode, it is possible to ensure sufficient analysis precision.

If the first mode is selected in analysis mode selection processing S4, the image processing unit 500 then performs second analysis processing S5. The second analysis processing is processing for acquiring the degree of oxygen saturation using the parameter N/W that is an indicator of absorption in the 550 nm band (specifically the N band). The non-volatile memory 532 of the controller 530 holds the numerical value table T2 (or function) that expresses the quantitative relationship between the total hemoglobin concentration tHb, the parameter N/W, and the degree of oxygen saturation Sat. Three numerical values (called a "numerical value set"), namely the total hemoglobin concentration tHb, the parameter N/W, and the degree of oxygen saturation Sat, are registered in association with each other in the numerical value table T2. In the second analysis processing S4, this numerical value table T2 is used to acquire the value of the degree of oxygen saturation Sat(x,y) for each pixel based on the G digital image data W(x,y) and N(x,y) acquired in processing S1 and the value of the total hemoglobin concentration tHb(x,y) acquired in first analysis processing S3.

Specifically, first, the parameter N/W(x,y) for each pixel (x,y) is calculated using Expression 16.

$$N/W(x,y)=N(x,y)/W(x,y) \qquad \text{Expression 16}$$

Next, for each pixel (x,y), the numerical value table T2 is referenced to extract the numerical value set that is closest to the value of the total hemoglobin concentration tHb(x,y) acquired in first analysis processing S3 and the value of the parameter N/W(x,y) calculated using Expression 16, and then the value of the degree of oxygen saturation Sat in the extracted numerical value set is read out and acquired as the value of the degree of oxygen saturation Sat(x,y) at that pixel (x,y).

If the second mode is selected in analysis mode selection processing S4, the image processing unit 500 performs third analysis processing S6. The third analysis processing is processing for acquiring the degree of oxygen saturation using the parameter R/(R+G+B) or R/W that is an indicator of absorption in the 600 to 700 nm band (wavelength region R4).

The non-volatile memory 532 of the controller 530 holds the numerical value table T3 (or function) that expresses the relationship between the parameter R/G and the correction value α shown in FIG. 5. This numerical value table T3 is used to acquire the correction value α for each pixel (x,y) based on the value of the parameter R/G(x,y).

The non-volatile memory 532 of the controller 530 also holds the numerical value table T4 (or function) that expresses the relationship between the parameter αR/(R+G+B) and the degree of oxygen saturation Sat shown in FIG. 4. The controller 530 uses Expression 17 to calculate the parameter αR/(R+G+B) for each pixel (x,y), and acquires the value of the degree of oxygen saturation Sat that corresponds to the calculated value of the parameter αR/(R+G+B) from the numerical value table T4.

$$\alpha \frac{R}{R+G+B}(x, y) = \frac{\alpha R(x, y)}{R(x, y) + G(x, y) + B(x, y)} \quad \text{Expression 17}$$

Also, instead of the parameter αR/(R+G+B), a configuration is possible in which the degree of oxygen saturation Sat is acquired using a parameter βR/W. The constant β is a correction value for removing the influence of the total hemoglobin concentration tHb from the parameter R/W, and corresponds to the correction value α. In this case, the numerical value table T3 expresses the relationship between the parameter R/G and the correction value β, and the numerical value table T4 expresses the relationship between the parameter βR/W and the degree of oxygen saturation Sat.

The non-volatile memory 532 of the controller 530 also stores a numerical value table (or function) that expresses the relationship between the degree of oxygen saturation Sat(x,y) and display colors (pixel values). Then, in processing S7, the controller 530 references this numerical value table (or function), and acquires pixel values that indicate the display colors corresponding to the degree of oxygen saturation Sat(x,y) obtained in the second analysis processing 5 or the third analysis processing S6.

The controller 530 then generates normal observation image data based on the R digital image data R(x,y), the G digital image data G(x,y), and the B digital image data B(x,y) that were obtained using illumination light IL (white light) that passes through the optical filter (ultraviolet cut filter) 418.

Figure 10:
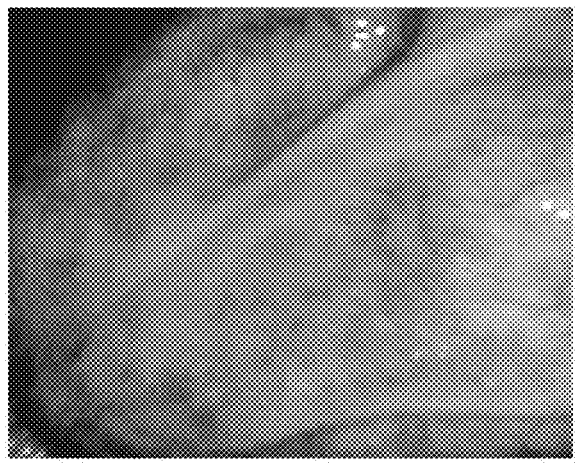
FIG. 10 shows an example of display of image information generated by the endoscope apparatus according to the embodiment of the present invention. (A) shows an example of a normal observation image, and (B) and (C) show an example of two-dimensional display of a degree of oxygen saturation distribution image.
Figure 10:
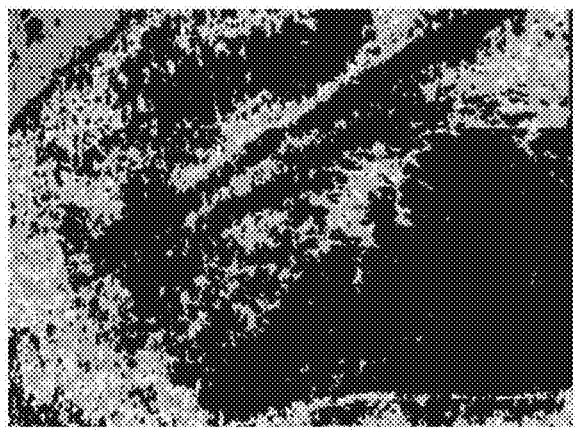
Figure 10:
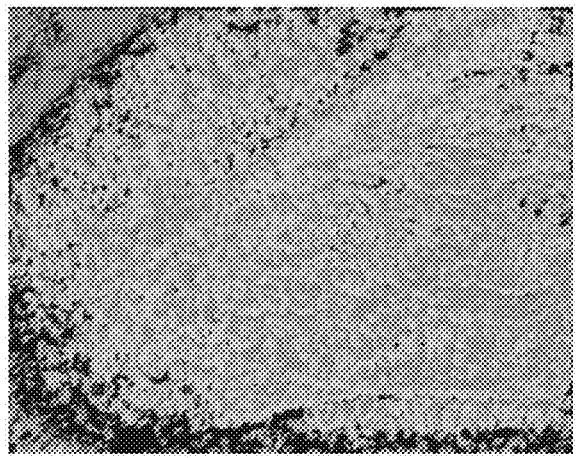

FIG. 10 shows an example of the display of image data generated by the controller 530. The controller 530 is one example of a feature amount distribution image generation unit. FIG. 10(A) is an example of the display of a normal observation image. FIG. 10(B) is an example of the display of degree of oxygen saturation distribution image data generated from the degree of oxygen saturation Sat(x,y) acquired by the second analysis processing S5 described above. Furthermore, FIG. 10(C) is an example of the display of degree of oxygen saturation distribution image data generated from the degree of oxygen saturation Sat(x,y) acquired by the third analysis processing S6 described above. Note that FIG. 10 shows the observation of the underside of a human tongue. In the degree of oxygen saturation distribution images in FIGS. 10(B) and 10(C), regions in which the value of the degree of oxygen saturation Sat(x,y) cannot be obtained with sufficient precision due to an insufficient amount of light are not displayed (i.e., are blacked out). In FIG. 10(B), the degree of oxygen saturation Sat(x,y) cannot be calculated with sufficient precision for almost all of the pixels (x,y) because the G digital image data N(x,y) captured using illumination light IL in the N band having a small light quantity is used in the calculation of the degree of oxygen saturation Sat(x,y), and therefore the majority of the region is not displayed. On the other hand, in FIG. 10(C), the degree of oxygen saturation Sat(x,y) is calculated with sufficient precision for almost all of the pixels (x,y) because image data captured using illumination light IL having a relatively larger light quantity is used in the calculation of the degree of oxygen saturation Sat(x,y), and therefore an image with gradation is rendered.

The controller 530 then uses the generated degree of oxygen saturation distribution image data and normal observation image data to generate screen data in which the normal observation image and the degree of oxygen saturation distribution image are displayed side-by-side in one screen, and stores the screen data in the video memory 540. Note that in accordance with a user operation, the controller 530 can generate various types of display screens, such as a display screen that displays only the degree of oxygen saturation distribution image, a display screen that displays only the normal observation image, or a display screen that displays supplementary information such as patient ID information and observation conditions in a superimposed manner on the degree of oxygen saturation distribution image and/or the normal observation image.

Malignant tumor tissue has a higher total hemoglobin concentration than normal tissue due to angiogenesis, and also exhibits remarkable oxygen metabolism, and therefore it is known that the degree of oxygen saturation Sat is lower than that of normal tissue. In view of this, the controller 530 can extract the pixels for which the total hemoglobin concentration acquired by first analysis processing S3 is greater than a predetermined reference value (first reference value), and for which the degree of oxygen saturation Sat acquired by second analysis processing S5 or third analysis processing S6 is less than a predetermined reference value (second reference value), perform enhanced display processing on corresponding pixels of normal observation image data for example to generate enhanced lesion site image data, and display the enhanced lesion site image on the monitor 300 along with the normal observation image and/or the degree of oxygen saturation distribution image (or on its own).

Examples of enhanced display processing include processing for increasing the pixel values of corresponding pixels, processing for changing the hue (e.g., processing for increasing the redness by increasing the R component, or processing for rotating the hue by a predetermined angle), and processing for flashing corresponding pixels (or periodically changing the hue).

Also, a configuration is possible in which, instead of generating enhanced lesion site image data, the controller 530 calculates an indicator Z(x,y) that indicates the degree of suspicion of a malignant tumor based on the deviation of the degree of oxygen saturation Sat(x,y) from an average value and the deviation of the total hemoglobin concentration tHb(x,y) from an average value, and generate image data in which the pixel values are the indicator Z (malignancy suspicion image data).

Although an embodiment of the present invention and specific working examples of the embodiment have been described above, the present invention is not limited to the above configuration, and various modifications can be made within the scope of the technical idea of the present invention.

Also, in the above embodiment, the present invention is applied to the analysis of the concentration distribution of hemoglobin in biological tissue, but the present invention can also be applied to the analysis of the concentration distribution of another biological substance (e.g., a secretion such as a hormone) that changes the color of biological tissue.

Also, the image sensor 141 of the present embodiment is described as an image sensor for color image capturing that includes R. G, and B primary-color color filters on the front side, but there is no limitation to this configuration, and an image sensor for color image capturing that includes Y, Cy, Mg, and G complementary-color color filters for example may be used.

Also, the image sensor 141 of the present embodiment is described as an image sensor for color image capturing that includes an on-chip color filter 141a, but there is no limitation to this configuration, and a configuration is possible in which, for example, an image sensor for black-and-white image capturing is used and includes a so-called frame sequential color filter. Also, the color filter 141a is not limited to having an on-chip configuration, and can be arranged in the optical path between the light source 430 and the image sensor 141.

Also, although the rotating filter 410 is used in the above embodiment, the present invention is not limited to this configuration, and another type of variable wavelength filter that enables switching the pass wavelength region can be used.

Also, in the above embodiment, a configuration is applied in which the rotating filter 410 is provided on the light source side and performs filtering on illumination light IL, but the present invention is not limited to this configuration, and a configuration is possible in which the rotating filter 410 is provided on the image sensor side (e.g., between the objective optical system 121 and the image sensor 131) and performs filtering on returning light from the subject.

Also, in the above embodiment, white light illumination light IL is used when capturing R digital image R(x,y) data for use in the third analysis processing S6, but a configuration is possible in which the rotating filter 410 is provided with an optical filter that accurately extracts the wavelength region R4, and the degree of oxygen saturation Sat is acquired based on R digital image data acquired under illumination by illumination light IL in the wavelength region R4 that passed through this optical filter. In this case, the pass wavelength region R4 of the optical filter can be set to a wavelength range from the isosbestic point E4 to 800 nm, but it is preferable that it is set to a wavelength range of 600 to 700 nm (particularly 650 to 650 nm) in which absorption is relatively high and sensitivity to the degree of oxygen saturation is high. For example, a configuration is possible in which the degree of oxygen saturation Sat is acquired based on R digital image data $R_{417}(x,y)$ acquired using illumination light IL that passed through the optical filter 417 of the above embodiment.

Also, in the above embodiment, a configuration is applied in which in the spectroscopic analysis mode, images are captured at a predetermined time interval while rotating the rotating filter 410 at a constant rotational frequency, but the present invention is not, limited to this configuration, and a configuration is possible in which, for example, the rotation position of the rotating filter 410 is changed in a stepwise manner at a predetermined time interval, and images are captured while the rotating filter 410 is in the stopped state.

Also, in the above embodiment, spectral analysis processing is performed using image data (RAW data) output from the image sensor, but it is possible to perform spectral analysis processing using image data that has been subjected to various types of image processing, such as interpolation processing (demosaic processing), linear matrix processing, white balance processing, or processing for color conversion to a predetermined color space (e.g., the sRGB space).

Also, in the above embodiment, a white light source such as a xenon lamp is used as the light source that generates wide band light for illumination, but it is possible to use a light source that generates non-white wide band light having a sufficient light quantity over the entire pass wavelength region of the optical filters that are used.

Also, although transmissive optical filters are used in the above embodiment, reflective optical filters that reflect a pass wavelength region may be used.

Also, although the above embodiment is an example of applying the present invention to an electronic endoscope apparatus that is one mode of a digital camera, the present invention is also applicable to a system that uses another type of digital camera (e.g., a digital single lens reflex camera or a digital video camera). For example, if the present invention is applied to a digital still camera, it is possible to observe body surface tissue or observe brain tissue during craniotomy (e.g., perform a rapid brain blood flow test).

The invention claimed is:

1. An endoscope apparatus comprising:

a light source apparatus;

an imager that generates RGB color image data by imaging biological tissue illuminated by light emitted by the light source apparatus; and a feature amount acquistioner that acquires a feature amount of the biological tissue based on the RGB color image data, wherein:

the feature amount acquistioner calculates a first parameter that has a correlation with a degree of oxygen saturation in the biological tissue based on the RGB color image data, the feature amount acquistioner acquires a corrected first parameter obtained by multiplying the first parameter by a first correction value for correcting influence of a total hemoglobin concentration, wherein the first correction value is based on a second parameter that has a correlation with the total hemoglobin concentration, if the total hemoglobin concentration that corresponds to a value of the second parameter is greater than or equal to a predetermined value, the feature amount acquisitioner calculates the degree of oxygen saturation based on the first parameter, if the total hemoglobin concentration that corresponds to the value of the second parameter is less than the predetermined value, the feature amount acquisitioner calculates the degree of oxygen saturation based on a third parameter that reflects absorption by hemoglobin in a 500 to 600 nm absorption band, the first parameter is any one of [a] and [b] below:
[a] R/(R+G+B)
[b] R/W
where
R is first normal observation image data R that is an R component of normal observation image data acquired under illumination by white light,
G is second normal observation image data G that is a G component of the normal observation image data,
B is third normal observation image data B that is a B component of the normal observation image data, and
W is first special observation image data W that is a G component of RBG color image data acquired under illumination by first special light, and the second parameter is any one of [c] to [e] below:
[c] R/G
[d] W/R
[e] W/(R+G)
where
R is the first normal observation image data R,
G is the second normal observation image data G, and
W is the first special observation image data W.

2. The endoscope apparatus according to claim 1, wherein the feature amount acquisitioner comprises a first storage that holds a numerical value table or a function that expresses a relationship between the corrected first parameter and the degree of oxygen saturation.

3. The endoscope apparatus according to claim 1, wherein the feature amount acquisitioner comprises a second storage that holds a numerical value table or a function that expresses a relationship between the second parameter and the total hemoglobin concentration.

4. The endoscope apparatus according to claim 1, wherein the feature amount acquisitioner acquires the total hemoglobin concentration based on the second parameter.

5. The endoscope apparatus according to claim 1, wherein the first special light has a wavelength from a vicinity of an isosbestic point E1 of hemoglobin appearing at 528±5 nm to a vicinity of an isosbestic point E4 appearing at 584±5 nm.

6. The endoscope apparatus according to claim 1,
wherein the light source apparatus comprises:
a white light source; and
a first optical filter that extracts the first special light from white light emitted by the white light source, and
the light source apparatus switches between emitting the white light and emitting the first special light.

7. The endoscope apparatus according to claim 6,
wherein the light source apparatus further comprises a second optical filter that extracts second special light from white light emitted by the white light source, and
the third parameter is N/W,
where
W is the first special observation image data W, and
N is the second special observation image data N that is a G component of RBG color image data captured under illumination by the second special light, and
the second special light has a wavelength from a vicinity of an isosbestic point E2 of hemoglobin appearing at 547±5 nm to a vicinity of an isosbestic point E3 appearing at 569±5 nm.

8. The endoscope apparatus according to claim 6, wherein the feature amount acquisitioner comprises a third storage that holds a numerical value table or a function that expresses a relationship between the third parameter and the degree of oxygen saturation.

9. The endoscope apparatus according to claim 1, comprising a feature amount distribution image generator that generates a feature amount distribution image that expresses a distribution of the feature amount in the biological tissue based on the feature amount.

10. The endoscope apparatus according to claim 1, wherein the imager is provided in a distal end portion of the endoscope.

11. An endoscope apparatus comprising:
a light source apparatus configured to generate first light and second light;
an imager that comprises an RGB color filter and configured to generate color image data by imaging biological tissue illuminated by light generated by the light source apparatus; and
a feature amount acquisitioner that acquires a feature amount of the biological tissue based on the color image data,
wherein first transmission light is a portion of the first light that passed through an R color filter of the imager, second transmission light is a portion of the second light that passed through a G color filter of the imager, and absorption by hemoglobin with respect to the first transmission light and the second transmission light has a correlation with a degree of oxygen saturation,
the feature amount acquisitioner has a selector that selects whether first image data acquired using the first transmission light or second image data acquired using the second transmission light is to be used to acquire a degree of oxygen saturation of the biological tissue, and
the feature amount acquisitioner acquires, based on the image data selected by the selector, a first parameter and a second parameter that has a correlation with a total hemoglobin concentration of the biological tissue,
if the total hemoglobin concentration that corresponds to a value of the second parameter is greater than or equal to a predetermined value, the selector selects acquisition of the degree of oxygen saturation based on the first image data,
if the total hemoglobin concentration that corresponds to the value of the second parameter is less than the predetermined value, the selector selects acquisition of the degree of oxygen saturation based on the second image data,
the first parameter is any one of [a] and [b] below:
[a] R/(R+G+B)
[b] R/W
where
R is first normal observation image data R that is an R component of normal observation image data acquired under illumination by white light,
G is second normal observation image data G that is a G component of the normal observation image data,
B is third normal observation image data B that is a B component of the normal observation image data, and
W is first special observation image data W that is a G component of RBG color image data acquired under illumination by first special light, and the second parameter is any one of [c] to [e] below:
[c] R/G
[d] W/R
[e] W/(R+G)

where
  R is the first normal observation image data R,
  G is the second normal observation image data G, and
  W is the first special observation image data W.

* * * * *